(12) United States Patent
Cantiani et al.

(10) Patent No.: US 6,509,176 B1
(45) Date of Patent: Jan. 21, 2003

(54) HETEROPOLYSACCHARIDE PRODUCED BY AN AGROBACTERIUM RADIOBACTER

(75) Inventors: Robert Cantiani, Lyons (FR); Alain Senechal, Charenton (FR); Sophie Vaslin, Saint-Cloud (FR); Paule Chevallereau, Melle (FR); Jean-Luc Simon, Melle (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/807,317

(22) PCT Filed: Oct. 8, 1999

(86) PCT No.: PCT/FR99/02416

§ 371 (c)(1),
(2), (4) Date: Jun. 25, 2001

(87) PCT Pub. No.: WO00/22154

PCT Pub. Date: Apr. 20, 2000

(30) Foreign Application Priority Data

Oct. 13, 1998 (FR) .............................................. 98 12832

(51) Int. Cl.⁷ .......................... C12P 19/04; C08B 37/00
(52) U.S. Cl. .......................... 435/101; 435/104; 435/72; 435/252.2; 536/123; 536/123.1; 536/126; 536/127
(58) Field of Search ................................. 435/101, 104, 435/72, 252.2; 536/123, 123.1, 126, 127

(56) References Cited

U.S. PATENT DOCUMENTS

| | | | |
|---|---|---|---|
| 4,247,639 A | 1/1981 | Kang | ......................... 435/101 |
| 5,236,046 A | 8/1993 | Robison | ..................... 166/270 |
| 5,252,727 A | * 10/1993 | Ullmann et al. | ............ 536/123 |

FOREIGN PATENT DOCUMENTS

| | | | |
|---|---|---|---|
| EP | 0 001 895 | 5/1979 | ........... C12D/13/04 |
| EP | 0 040 445 | 11/1981 | ........... E21B/43/00 |
| EP | 0 042 714 | 12/1981 | ........... C12P/21/04 |
| EP | 0 138 255 | 4/1985 | ........... C12P/19/04 |
| EP | 0 351 303 | 1/1990 | ........... C12P/19/04 |
| EP | 0 725 143 | 8/1996 | ........... C12D/13/04 |
| WO | WO 94/06927 | 3/1994 | ........... C12P/19/04 |

OTHER PUBLICATIONS

Qian et al, Biological Abstracts, Accession No. 1985:383056, 1985.*
International Search Report (2000).

* cited by examiner

Primary Examiner—Francisco Prats

(57) ABSTRACT

The invention concerns a heteropolysaccharide (HP) characterised in that it is obtainable by fermenting in a medium comprising at least an *Agrobacterium radiobacter* I-2001 (or DSM 12095) strain, one of its recombinants, or one of its mutants, and a carbon source capable of being assimilated by said strain, one of its recombinants or one of its mutants. The invention also concerns a method for preparing said heteropolysaccharide and its use as thickening and/or gelling agent.

28 Claims, No Drawings

HETEROPOLYSACCHARIDE PRODUCED BY AN AGROBACTERIUM RADIOBACTER

This application is an application under 35 U.S.C. Section 371 of International Application Number PCT/FR99/02416 filed on Oct. 8, 1999.

The present invention relates to a heteropolysaccharide (HP) characterized in that it can be obtained by fermentation of a medium including at least one *Agrobacterium radiobacter I*-2001 (or DSM 12095) strain, a recombinant thereof or mutant thereof, and a source of carbon which can be assimilated by said strain, a recombinant thereof or a mutant thereof.

In many industrial domains, there is a constant search for novel compounds with:
improved rheological properties, and which are capable of forming gels,
increased compatibility with the media into which they are incorporated,
great stability over a wide temperature and pH range.

In the case of compounds obtained at the end of a bacterial fermentation, it is also important for the compound to have good productivity.

The ability to gel is very advantageous since they are systems which are particularly attractive by virtue of the diversity of the domains in which they have applications: some applications require the use of a gel.

Thus, for example, the agrofoods industry provides a wide range of gelled products (creams, yoghurts, diverse jellies, ice creams, etc.), and the pharmaceutical industry uses gels as active principle or thickening agent supports.

In entirely another domain, some paints do not drip since they have gel characteristics when standing, whereas they spread easily with a paintbrush (rheofluidifying profile).

Aqueous gels are also used as chromatographic supports or for developing contact lenses.

Heteropolysaccharides of bacterial origin, such as for example xanthan gum, have already been described and used for their effective rheological properties under extreme temperature and pH conditions. However, these heteropolysaccharides, which are suitable in applications in solution, do not always produce gels.

It is known that the gelling of a medium takes place when a three-dimensional network is formed subsequent to the crosslinking of the components of said medium.

Conventionally, this gelling is brought about by adding additional cations in particular of alkali metal or alkaline earth metal type (for example calcium and/or magnesium) to the medium, by switching the pH toward acid or basic pHs, by adding another compound, in particular another polysaccharide (for example the combination of xanthan and carob), or by modifying the temperature.

Whatever the application envisaged, the abovementioned gelling conditions may:
harm the stability and the compatibility of the final gel due to the interactions between the additional cations or the coadditive, which must be introduced in order to obtain the gel, and the other ingredients present in said compositions, or
denature the heteropolysaccharide and/or the other ingredients present in said compositions due to the high temperatures and/or the pH changes.

In the context of the present invention, the term "gel" refers to a pseudosolid (behavior close to a solid) resulting from the association, at least partial, of heteropolysaccharide chains dispersed in a liquid. In a stressing frequency range $\omega$, the pseudo-solid gels are in general characterized, with regard to their solid component, by an elastic modulus $G'(\omega)$ also called storage modulus and, with regard to their liquid or viscous component, by a viscous modulus $G''(\omega)$ also called loss modulus.

The mechanical values $G'(\omega)$ and $G''(\omega)$ can be measured using a controlled strain rheometer and operating in oscillatory mode. By way of nonlimiting indication, mention may be made, for example, of a Rheo-Fluid Spectrometer® rheometer.

$G'$ and $G''$ can also be measured on a controlled stress rheometer and operating in oscillatory mode. By way of indication, mention may be made, for example, of a CAR-RIMED® rheometer.

The principle of the measurement consists in determining, firstly, the range of reversible mechanical strain in which the response of the gel to the mechanical stressing is linear as a function of said strain. Secondly, the gel is subjected to a set value of mechanical strain included in the linear range determined above. The rheometer then carries out a frequency sweep $\omega$.

The stress response of the gel which is in phase with the strain gives the elastic modulus $G'(\omega)$. $G'(\omega)$ corresponds to the energy stored by the gel in elastic form and can be recovered.

The stress response of the gel which is out of phase by an angle of 90° with the strain gives the viscous modulus $G''(\omega)$. $G''(\omega)$ corresponds to the energy dissipated by the viscous flow and can not be recovered.

A gel is termed strong or true when, throughout the stressing frequency range ($\omega$) swept, the $G'/G''$ ratio is greater than or equal to 10, i.e. when the elasticity of the gel remains high and when the value of $G'(\omega)$ is greater than or equal to 10 Pa.

The aim of the present invention is precisely to provide heteropolysaccharides which have very good rheological properties, in particular in terms of thickening and pseudoplastic (rheofluidifying) properties, and also the ability to produce true gels without adding additional cations to the medium and without switching the pH, this being at temperatures lower than or equal to 40° C.

The aim of the present invention is also to provide a heteropolysaccharide with very good rheological properties at low concentrations.

The present invention therefore relates to a heteropolysaccharide (HP) characterized in that it can be obtained by fermentation of a medium including at least one *Agrobacterium radiobacter I*-2001 (or DSM 12095) strain, a recombinant thereof or a mutant thereof, and a source of carbon which can be assimilated by said strain, a recombinant thereof or a mutant thereof.

The *Agrobacterium radiobacter* strain was deposited in accordance with the Treaty of Budapest, with the Collection Nationale de Culture des Micro-organisms (CNCM) [National Collection of Microorganism Cultures], on Apr. 3, 1998, where it can be accessed publicly under the number I-2001. It was also deposited with the Deutsche Sammlung von Mikro-organismen und Zellculturen GmbH (DSMZ), on Apr. 21, 1998, where it can be accessed publicly under the number DSM 12095.

Pure culturing of *Agrobacterium radiobacter I*-2001 (or DSM 12095) can be carried out in Petri dishes incubated at a temperature of between 25° C. and 30° C., and more particularly of between 25° C. and 28° C., for approximately 24 hours.

The sources of carbon and nitrogen which can be assimilated by *Agrobacterium radiobacter I*-2001 (or DSM 12095) can be chosen from glucose, fructose, galactose, trehalose, mannose, melobiose, sucrose, raffinose, maltotriose, maltose, lactose, lactulose, methyl-β-galactopyranoside, methyl-α-galactopyranoside, cellobiose, gentobiose, methyl-β-D-glucopyranoside, methyl-α-D-glucopyranoside, esculin, ribose, arabinose, xylose, palatinose, rhamnose, fucose, melezitose, D(+) arabitol, L(−) arabitol, xylitol, dulcitol, tagatose, glycerol, myo-innositol, mannitol, maltitol, turanose, sorbitol, adonitol, lyxose, erythritol, D(−) tartrate, D(+) malate, L(−) malate, cis-aconitate, trans-aconitate, 2-keto-D-gluconate, N-acetylglucosamine, guinate, betaine, succinate, fumarate, glycerate and glucosamine.

Among the possible maintenance media for the strain, the maintenance medium of the type Difco MY agar (reference 0712-01-8) is considered to be particularly advantageous. Said Difco MY agar medium has the following composition:

| | |
|---|---|
| bacto-yeast extract | 3 g |
| malt extract | 3 g |
| bacto-peptone | 5 g |
| bacto-dextrose | 10 g |
| bacto-agar | 20 g |

For conserving the strain, it is preferable to anticipate at least one preculturing step. The term "preculturing step" is intended to mean a step which consists in developing and multiplying the bacterial strain, without polysaccharide production.

It has been possible to demonstrate that, in general, the heteropolysaccharide (HP) includes glucose motifs and/or derivatives thereof, galactose motifs and/or derivatives thereof, glucuronic acid motifs and/or salts thereof, acetic acid motifs and/or salts thereof, and pyruvic acid motifs and/or salts thereof.

The constituent motifs of the heteropolysaccharide (HP) are in general present in molar proportions as follows, taking, as a reference, glucose to be equal to 1:

galactose and/or derivatives thereof 0.2–5,
glucuronic acid and/or salts thereof 0.1–3,
acetic acid and/or salts thereof 0–5,
pyruvic acid and/or salts thereof 0.01–2.

More particularly, said motifs are present in molar proportions as follows, taking, as a reference, glucose to be equal to 1:

galactose and/or derivatives thereof 0.5–4, and preferably 0.8–2,
glucuronic acid and/or salts thereof 0.2–2, and preferably 0.4–1,
acetic acid and/or salts thereof 0–4, and preferably 0–3,
pyruvic acid and/or salts thereof 0.01–2.

The glucuronic, acetic and pyruvic acids can be in the form of salts. By way of salts, mention may be made of sodium, potassium, calcium or ammonium salts.

The principle of the methods of analysis of the heteropolysaccharide (HP) which have made it possible to determine its crude formula as specified above is the determination of the constituent elements (monosaccharides and acids) after hydrolysis of said heteropolysaccharide (HP) and chromatographic assays with internal or external calibration.

Thus, the monosaccharide assay was carried out in the following way: 100 mg of heteropolysaccharide (HP) are hydrolyzed in hermetic tubes with 5 ml of molar trifluoroacetic acid at 105° C. for three to six hours.

This operation is followed by evaporation to dryness and taking up the dry residue in 5 ml of pyridine containing 15 mg of sorbitol as an internal standard; then silylation on 1 ml of pyridine solution, with 0.9 ml of hexamethyldisilazane. The silylation is catalyzed with 0.1 ml of trifluoroacetic acid.

The monosaccharide assay is then carried out by FID (Flame Ionization Detection) gas phase chromatography, on a glass capillary column 25 meters long and 0.25 mm in diameter, loaded with methylsilicone phase having a film thickness of 0.14 microns. The gas vector used is hydrogen, with a flow rate of 2 ml/minute.

The pyruvic acid assay is carried out using a stock solution obtained by hydrolyzing 50 mg of heteropolysaccharide (HP) using 5 ml of 1N hydrochloric acid for 1 hour at 105° C., then adding 2 mg of ketoglutaric acid (constituting the internal standard) and adjusting to 25 ml with distilled water. This operation is followed by reaction with 2,4-dinitrophenylhydrazine (DNPH):

1 ml of solution of DNPH at 7 mg/ml in 2N HCl is added to 1 ml of the above solution;
the reaction time is 5 minutes; then
2 ml of acetone and 6 ml of water-acetonitrile mixture are added.

The assay is then carried out by High Performance Liquid Chromatography (HPLC) using a column loaded with 5 micron diameter C-18 grafted silica, the length of which is 250 mm and the diameter of which is 4.6 mm. The eluant used is a 50/50 mixture by volume of 0.02 mol/l phosphoric acid and of acetonitrile. The flow rate is 2 ml/minute.

The detection of the pyruvic acid is carried out using ultraviolet light at 375 nm.

The acetic acid assay takes place after hydrolysis of 100 mg of heteropolysaccharide (HP) with 5 ml of 2N hydrochloric acid at 105° C. for one hour. 5 ml of a solution of propionic acid at 5 mg/ml are then added as an internal standard, and 15 ml of demineralized water are added to the mixture. The assay is carried out by HPLC using a 5 micron C-18 grafted silica column, 250 cm in length and 4.6 mm in diameter. The eluant is a 0.02 mol/l aqueous phosphoric acid solution at a flow rate of 1.2 ml/minute. The detection is refractometric.

The glucuronic acid is assayed via the $CO_2$ released by the decarboxylation subsequent to the treatment, while hot, of the gum with hydrochloric acid according to the method described in the Food Chemical Codex, 4th edition, page 768.

The molar mass by weight is determined by exclusion chromatography on TSK PW 4000 and 6000 columns in series (columns 30 cm in length and 7 mm in diameter), with refractometric detection. The eluant is a 0.1 mol/l sodium nitrate solution. The heteropolysaccharide is at approximately 0.015% by weight in the eluant. The calibration is carried out using pullulanes, which are monodispersed polysaccharides of molar masses of between $5 \times 10^3$ and $1.6 \times 10^6$ g/mol extrapolated up to $10^7$ g/mol.

The mean molar mass by weight (Mw) is obtained from the mass distribution curve derived from the chromatogram; it is generally between $1 \times 10^5$ and $5 \times 10^6$ g/mol, preferably between approximately $8 \times 10^5$ and $5 \times 10^6$ g/mol. The mean molar mass by weight is more particularly approximately $3 \times 10^6$ g/mol.

As already mentioned, the (HP) has very good rheological properties in solution, in particular in distilled water or mains water.

Thus, it could be noted that, for example, 1% weight/weight solutions of (HP) in distilled water at 23° C., and at a frequency of 1 Hz, produce G' values of between 0.1 and 200 Pa and G" values of between 0.1 and 20 Pa.

(HP) produces strong or true gels when the G' and G" values are advantageously between 20 and 200 Pa for G' and between 0.5 and 15 Pa for G". Even more advantageously, G' is between 20 and 150 Pa and G" between 0.5 and 10 Pa. According to a particularly preferred embodiment, the G' value is approximately 100 Pa and that of G" is approximately 5 Pa (in distilled water).

The (HP) confers viscosity on the aqueous medium, which is evaluated by flow rheology. The rheological measurements of flow viscosity are carried out using a controlled stress rheometer or controlled shear rate rheometer, such as for example using a viscosimeter of RHEOMAT® or CAR-RIMED® type, respectively.

In both cases, the apparatus measures the stress upon flowing of the HP+water mixture when this mixture is irreversibly strained. The flow viscosity is calculated from the stress.

This apparatus thus makes it possible to quantify the viscosity level at a given shear rate.

The flow viscosity can be more simply evaluated using a BROOKFIELD® viscosimeter.

These rheological measurements of (HP) flow viscosity make it possible, in addition, to evaluate the flow threshold of the (HP) solution and/or of the formulation comprising it. Said threshold represents the strength which must be provided in order to destroy the structure of the medium and to force it to flow.

The flow rheology also makes it possible to quantify the ease with which an (HP) solution and/or a formulation comprising it flows when the controlled shear increases (pseudoplastic or rheofluidifying behavior).

It was noted, for example, that 1% weight/weight solutions of HP in distilled water containing 1% weight/weight of NaCl, at 23° C., produces flow viscosity values, at a shear rate of $0.1\ s^{-1}$, of between 100 and 5000 Pa·s, and more particularly of between 200 and 2000 Pa·s.

Under similar conditions, at a shear rate of $10\ s^{-1}$ flow viscosity values of between 0.5 and 300 Pa·s, and more particularly between 5 and 150 Pa·s are produced.

These flow rheology data are representative of the behavior of the formulation when it is masticated, when it is poured, when it is overrun, etc.

The gels obtained by incorporating (HP) into the medium are cicatrizing gels, i.e. after shearing, even strong shearing, the "fractured" gels have the power of reforming and of recovering their initial properties.

The cicatrizing power of the gels obtained from (HP) is evaluated using compression testing measurements carried out, for example, on an ETIA T2 texturizer composed of a cylindrical measuring body 12.7 mm in diameter, with a penetration rate of 0.05 mm/s and a penetration height of 15 mm. The plunger is pushed into the gel at the same place several times, at different time intervals, and the compression strength is recorded. The slope at the origin expressed in mN/mm, representative of the elasticity of the gel, is determined.

For example, a gel is prepared with 1% weight/weight of (HP) in distilled water. This gel is then stored for 24 hours before carrying out the compression testing measurements, either at room temperature (approximately 25° C.) or in the cold at approximately 6° C.

Compression testing measurements are carried out at different time intervals: 0, 5, 15 minutes and 24 hours, with a 5 minute gap between each measurement.

Thus, the slope remains constant is approximately equal to 45±1 mN/mm, whatever the measurement time (t=0, 5, 15 minutes and 24 hours).

This means that the elasticity of the gel is stable and that it has the power to cicatrize several times in succession over time, while at the same time maintaining the same gel strength.

The present invention also relates to a process for preparing the heteropolysaccharide (HP) as defined above.

The preparation process consists, firstly, of the fermentation of a medium including at least one source of carbon which can be assimilated by an *Agrobacterium radiobacter* I-2001 (or DSM 12095) strain, a recombinant thereof or a mutant thereof.

Besides said source of carbon which can be assimilated, the fermentation medium can also contain at least one organic or inorganic source of nitrogen, and optionally one or more inorganic salts.

The medium is inoculated conventionally with the *Agrobacterium radiobacter* I-2001 (or DSM 12095) strain.

By way of an organic source of carbon which is a constituent of the fermentation medium, besides the sugars mentioned above, mention may also be made of sugars such as starch, advantageously hydrolyzed, starch hydrolysates, the mixtures of these sugars and the mixtures comprising at least one of these sugars.

More particularly, mention may be made of glucose, sucrose, starch, advantageously hydrolyzed, starch hydrolysates, lactose, the mixtures of these sugars and the mixtures comprising at least one of these sugars. Glucose and sucrose are the sugars which are even more preferred.

The carbon source concentration in the fermentation medium can be between 1 and 100 g/l, and preferably between 15 and 60 g/l.

By way of organic source of nitrogen, mention may be made of casein and caseinates, fish hydrolysates, wheat, corn or soya flours, yeast extracts (bakers' yeast, brewers' yeast, lactic yeasts, etc.), corn steap liquor (CSL), urea and potato proteins.

By way of inorganic sources of nitrogen, mention may be made of ammonium or sodium nitrates, and ammonium phosphates or sulfates.

The fermentation can also take place with a mixture of organic and inorganic sources of nitrogen.

The nitrogen-containing source (organic, inorganic or a mixture of the two) concentration in the fermentation medium can be between 1 and 80 g/l, preferably between 3 and 50 g/l.

The fermentation medium can also contain trace elements, such as traces of iron and/or of calcium and/or of manganese and/or of magnesium salts, and also vitamins and nucleotides.

The fermentation can be carried out at pressures of between 1 and 4 bar, at a temperature of between 25° C. and 35° C., preferably of between 25° C. and 30° C., under aerobic conditions.

The pH of the fermentation medium can be between 5 and 9, and preferably between 6 and 8. The pH can be adjusted, depending on the case, with a base such as sodium hydroxide, potassium hydroxide or aqueous ammonia, or with an acid such as sulfuric acid, phosphoric acid, hydrochloric acid or nitric acid.

The fermentation medium, placed in a fermentation tank or container, can be advantageously subjected to agitation. This agitation can be carried out, for example, using a reciprocal shaker, a rotary shaker, a stirring spindle or a column of bubbles. The fermentation time is conventionally longer than 30 hours, but generally between 40 and 100 hours.

The fermentation yields are generally greater than 40%, more particularly between 55 and 75% and most particularly between 60 and 75% by weight of heteropolysaccharide (HP) produced with respect to the source of carbon used.

After fermentation, the heteropolysaccharide (HP) can be separated from the fermentation must according to the following steps:

i—the end-of-fermentation must is subjected to heat treatment between 80° C. and 120° C. for 10 to 60 minutes,
ii—the heteropolysaccharide (HP) is precipitated using an at least partially water-miscible organic liquid,
iii—the heteropolysaccharide (HP) is separated from the organic liquid.

In step (i), the fermentation must containing the heteropolysaccharide (HP) is advantageously heated at temperatures of between 80° C. and 120° C. for 10 to 60 minutes, and preferably for between 15 and 45 minutes.

The must subjected to the heat treatment above advantageously has a pH of between 6 and 8.

However, this pH can be adjusted if necessary, depending on the case, with a base or acid.

The latter can be chosen from the bases and acids mentioned above, used for adjusting the pH of the fermentation medium.

According to a preferred variant of the invention, the must derived from step (i) is maintained at the same temperature as the temperature of the heat treatment.

In step (ii), the heteropolysaccharide (HP) is recovered from the must obtained in step (i), advantageously by precipitation using an organic liquid which is at least partially water-miscible and in which the heteropolysaccharide (HP) is insoluble or practically insoluble.

By way of liquids which are suitable according to the present invention, mention may be made of acetone or alcohols which include 1 to 6 carbon atoms, such as ethanol, propanol, isopropanol, butanol, tert-butanol, or the mixture thereof.

More particularly, the precipitation of (HP) is carried out with isopropanol.

The volume of organic liquid used is generally at least twice that of the volume of must to be treated.

The precipitation of the heteropolysaccharide (HP) with an organic liquid can also be carried out in the presence of salts, such as sodium, potassium or calcium sulfates, chlorides or phosphates.

According to a particular embodiment, the precipitation can take place at a temperature of between 40 and 60° C.

The heteropolysaccharide (HP), once precipitated, can then be separated, in step (iii), from the organic liquid.

The separation method is not critical in itself, and can be chosen equally from the usual known separation methods, such as for example filtration, centrifugation or spin-filtering.

The fibers obtained can be optionally dehydrated, for example using acetone or an alcohol such as ethanol, propanol or isopropanol.

The weight of alcohol required to carry out this dehydration operation is generally 1 to 10 times that of the fibers to be treated.

The dehydrated fibers can undergo further filtration, centrifugation or spin-filtering operations.

Where appropriate, the fibers can be dried, ground and/or sieved so as to obtain a heteropolysaccharide (HP) powder.

If the intention is to obtain a purer powder, it is possible to treat either the fermentation must or an aqueous solution reconstituted from the powder obtained according to the process described above, using one or more enzymes.

By way of enzymes which may be suitable for this purpose, mention may be made of proteases, mutanases, lipoproteases, cellulases and chitinases.

The enzymatic purification can be combined or replaced with physical purification processes, such as the various filtration, centrifugation or dialysis methods, or with various chromatographic techniques.

The fermentation musts and the reconstituted solutions of heteropolysaccharide (HP), possibly having undergone purification treatment, can be concentrated.

Concentration can be advantageous in certain cases, in particular when the transport costs can thus be decreased. In addition, the concentrated solutions can be more rapidly used than the heteropolysaccharide (HP) powders.

The concentration can be carried out by all the techniques known to those skilled in the art, in particular evaporation, ultrafiltration or diafiltration.

In the present invention, the heteropolyaccharide (HP) is advantageously present in the form a solid of fiber or powder type.

As already mentioned, (HP) has very good rheological properties, and in particular the ability to form true gels. Depending on the fermentation conditions, in particular depending on the components and the concentrations thereof in the culture medium, and/or the precipitation conditions in step (ii) of the process (more particularly whether or not the precipitation takes place in the presence of salts), (HP) has the advantage of being able to be used as a thickening agent or as a gelling agent, or both.

Thus the present invention relates to the use of the heteropolysaccharide (HP) as described above or as obtained by the process defined above, as a thickening and/or gelling agent.

(HP) can be used as a thickening and/or gelling agent, for example in the petroleum, agrochemical, food, cosmetics, paper and textile industries, and also in paints, contact lenses, glues, inks and household or industrial cleaners.

The amount of heteropolysaccharide (HP) of the invention which can be used in cosmetic compositions depends on the aqueous medium to be thickened and/or to be gelled. This amount can represent from 0.01% to 5% approximately, preferably about 0.1% to 0.3%, of the weight of the thickened or gelled aqueous medium.

The term "cosmetic composition or formulation" is intended to mean all the cosmetic products or preparations such as those described in annex 1 ("Illustrative list by category of cosmetic products") of European directive No. 76/768/EEC of Jul. 27, 1976, termed cosmetic directive.

The cosmetic compositions can be formulated into a large number of types of products for the skin and/or the hair, such as mousses, gels (in particular styling gels), conditioners, formulations for hair styling or for facilitating the combing of hair, rinsing formulations, hand and body lotions, products which regulate skin moisturization, cleansing milks, make-up-removing compositions, creams or lotions for protection against the sun and ultraviolet rays, care creams, anti-acne preparations, local analgesics, mascaras, products intended to be applied to the lips or other mucous membranes, sticks and other compositions of the same type.

These cosmetic compositions make use of a vehicle, or of a mixture of several vehicles, present in said compositions at concentrations of between 0.5% and 99.5% approximately, generally between 5 and 90% approximately.

The choice of the suitable vehicle depends on the nature of the ingredients used and on the destination of said compositions, depending on whether the formulated product is supposed to be left on the surface to which it has been applied (for example sprays, mousses, tonic lotion or gels) or, on the other hand, rinsed after use (for example, shampoo, conditioner, rinsing lotions).

The aqueous vehicles present in the cosmetic compositions can also contain $C_1$–$C_6$ alcohols, in particular methanol, ethanol and isopropanol. They can also contain another solvent making it possible to solubilize or disperse, in the aqueous medium, the various ingredients used in said compositions.

Said vehicles can thus also contain a large variety of other solvents, such as acetone, hydrocarbons, halohydrocarbons, linalool volatile silicones and esters. The various solvents which can be used in the aqueous vehicles may or may not be miscible with each other.

When the cosmetic compositions are in the form of sprays, tonic lotions, gels or mousses, the preferential vehicles comprise, besides water, ethanol, volatile derivatives of silicone, and mixtures thereof.

The formulations for aerosol sprays and mousses can also contain a propellant capable of generating the products in the form of mousse or fine sprays, which are uniform. By way of examples, mention may be made of trichlorofluoromethane, dichlorodifluoromethane, difluoroethane, dimethyl ether, propane, n-butane or isobutane.

Said aqueous vehicles can have a large number of forms, in particular those of emulsions, including the water-in-oil emulsions, oil-in-water emulsions, and multiple emulsions, the desired viscosity of which can range up to 2000000 mpa·s.

Besides the aqueous vehicle, the cosmetic compositions can contain surfactants, used to disperse, emulsify, solubilize and stabilize various compounds used in particular for their emollient or wetting properties. They can be of anionic, nonionic, cationic, zwitterionic or amphoteric type; by way of examples, mention may be made of:

anionic surfactants in an amount which can range from 3% to 50%, preferably from 5% to 20%, agents such as
- alkyl ester sulfonates
- alkyl sulfates
- alkylamide sulfates
- salts of saturated or unsaturated fatty acids nonionic surfactants in an amount which can range from 0.1% to 30%, preferably from 2% to 10%, agents such as
- polyoxyalkylenated alkylphenols
- glucosamides, glucamides
- glycerolamides derived from N-alkylamines
- polyoxyalkylenated $C_8$–$C_{22}$ aliphatic alcohols
- the products resulting from the condensation of ethylene oxide with a hydrophobic compound resulting from the condensation of propylene oxide with propylene glycol,
- amine oxides
- alkylpolyglycosides and the polyoxyalkylenated derivatives thereof
- amides of $C_8$–$C_{20}$ fatty acids
- ethoxylated fatty acids
- ethoxylated amidoamines, amines, amides amphoteric and zwitterionic surfactants in an amount which can range from 0.1% to 30%, preferably from 1% to 10%, agents such as
- those of betaine type such as
  - betaines
  - sulfobetaines
  - amidoalkylbetaines
  - and sulfobetaines
- alkylsultaines
- the products of condensation of fatty acids and of protein hydrolysates,
- cocoamphoacetates and cocoamphodiacetates
- alkylampho-propionates or -dipropionates,
- amphoteric derivatives of alkylpolyamines Conditioners can also be present, in an amount which can range from 0.05% to 5%, preferably from 0.1% to 1%. Among these, mention may be made of those of synthetic origin which are better known under the name polyquaternium, such as the polyquaterniums -2, -7 and -10, the cationic derivatives of polysaccharides, such as hydroxyethyl cocodimonium cellulose, guar hydroxypropyl trimonium chloride, hydroxypropyl guar hydroxypropyl trimonium chloride, the nonvolatile derivatives of silicones, such as amodimethicone, cyclomethicones, non-water-soluble and nonvolatile organopolysiloxanes, such as-oils, resins or gums such as diphenyldimethicone gums.

The cosmetic compositions can also contain polymers with film-forming properties which can be used to provide an attaching function. These polymers are generally present at concentrations of between 0.01 and 10%, preferably of between 0.5 and 5%. They are preferably of the type polyvinylpyrrolidone, copolymers of polyvinylpyrrolidone and of methyl methacrylate, copolymers of polyvinylpyrrolidone and of vinyl acetate, polyethylene glycolterephthale/polyethylene glycol copolymers, and sulfonated terephthalic copolyester polymers.

The cosmetic compositions can also contain polymeric derivatives which exert a protective function, in amounts of about 0.01–10%, preferably approximately 0.1–5% by weight, derivatives such as
- cellulose derivatives
- polyvinyl esters grafted onto polyalkylene trunks
- polyvinyl alcohols
- sulfonated terephthalic copolyester polymers
- ethoxylated monoamines or polyamines, polymers of ethoxylated amines The performances of the cosmetic compositions can also be improved by using plasticizers in an amount which can range from 0.1 to 20% of the formulation, preferably from 1 to 15%. Among these agents, mention may be made of adipates, phthalates, isophthalates, azelates, stearates, silicon copolyols, glycols, castor oil, or the mixtures thereof.

It is also possible to advantageously add to these compositions metal-sequestering agents, more particularly those which sequester calcium, such as citrate ions, or polymeric dispersing agents in an amount of about 0.1–7% by weight, in order to control the calcium and magnesium hardness, agents such as
- water-soluble salts of polycarboxylic acids
- polyethylene glycols of molecular mass of about 1000 to 50000.

It is also possible to incorporate into the cosmetic compositions wetting agents; mention may be made of glycerol, sorbitol, urea, collagen, gelatin and emollients which are generally chosen from alkylmono-glycerides and alkyldiglycerides, triglycerides, such as oils extracted from plants and from vegetables or oils of animal origin or the hydrogenated derivatives thereof, mineral oils or liquid paraffins, diols, fatty esters and silicones.

To these compounds, it is possible to add, in combination, inorganic particles or powders such as calcium carbonate, inorganic oxides in the form of powder or in colloidal form such as titanium dioxide, silica, aluminum salts, kaolin, talc, clays and the derivatives thereof.

One or more fragrances, dyes and/or opacifyers such as pigments are generally added to these ingredients.

In order to protect the skin and/or hair against attacks from the sun and from UV rays, it is possible to add to these formulations sunscreens which are either chemical compounds which strongly absorb UV radiation, or inorganic particles such as zinc oxide, titanium dioxide or cerium oxides.

Preserving agents, such as p-hydroxybenzoic acid esters, sodium benzoate or any chemical agent which prevents bacterial proliferation or the proliferation of molds and which is conventionally used of the cosmetic compositions are generally introduced into these compositions to an amount of 0.01 to 3% by weight.

Agents which modify the activity of water and which greatly increase osmotic pressure, such as carbohydrates or salts, can sometimes be used.

The cosmetic composition can also contain other viscosity modifying and/or gelling polymers, such as crosslinked polyacrylates, hydrocolloids obtained by fermentation, such as xanthan gum and Rheozan, cellulose derivatives, such as hydroxypropylcellulose or carboxymethylcellulose, guars and the derivatives thereof, etc., used alone or in combination.

The invention relates more particularly to the use of the heteropolysaccharide as a thickening and/or gelling agent in dietary formulations.

The dietary formulations to which the heteropolysaccharide (HP) is added are conventionally simple or multiple liquid emulsions, complex gas and liquid emulsions (overrun systems), suspensions of liquids and solids, or any other system combining these possibilities.

In these formulations, the liquid is advantageously water or a liquid comprising water, at least in part.

The dietary formulations are obtained by implementing the conventional methods for preparing dietary formulations according to their type. Thus, the (HP) advantageously in the form of a solid of fiber or powder type is mixed with the other ingredients required for the formulation. The entire mixture can, where appropriate, be homogenized.

The temperature at which the formulation is prepared is not critical in itself. The formulations comprising the (HP) can be sterilized without any damage to their properties for use. Another advantage of (HP) is that it is possible to prepare the dietary formulations without having to heat the ingredients beforehand.

(HP) remains compatible despite the diversity of the dietary formulations (pH, ionic strength, composition), and substantially conserves its properties.

The advantageous rheological properties associated with the heteropolysaccharide (HP) which is the subject of the invention, and also the ability of the latter to produce true gels at temperatures lower than or equal to 40° C., this being within a wide pH range, also makes it possible to confer on the formulations in which it is used alone or in combination with other additives a texture close to that of the formulations comprising exclusively said additives.

The measurable parameters for characterizing the texture of the dietary formulations are rheological in nature, and consist essentially in measuring the elastic (G') and viscous (G") moduli, and the flow viscosity at a given shear rate. G' and G", and also the viscosity, have been defined above.

The objective of these rheological characteristics is to demonstrate the visco-elastic and/or pseudoplastic behaviors of the formulations, in order to compare them to each other.

(HP), advantageously in the form of a solid of fiber or powder type, has the ability to confer a rheofluidifying profile on the formulation comprising it.

(HP) has, similarly, the ability to produce true gels which can cicatrize after application of a mechanical stress.

It should be noted that the G' and G" moduli, and also the viscosity, measured for a formulation can be different from those measured for (HP) in distilled water.

In milk-based and set desserts, such as, for example, flans, it is possible to advantageously replace, at least partially, the usual gelling agents, in particular gelatin, with (HP).

In salty-acid media, such as vinaigrettes, the aqueous medium contained can be structured by adding small amounts of (HP).

In the field of confectionery, in particular in gum confectioneries of the HARIBO® type, it is possible to advantageously replace, at least partially, the gelling agents, such as for example gelatin, with (HP).

In media with high ionic strength, in particular in pork-butchery, (HP) can be added to the carrageenans in order to reinforce the texture, in particular the elastic appearance of sausages, for example.

In formulations intended to be overrun, such as Chantilly creams, toppings or ice creams, (HP) can be used as a thickening and/or gelling agent.

Similarly, (HP) can be used in formulations such as mayonnaises, vegetable mousses or mousses comprising proteins, for instance meat or fish mousses, or mousses comprising albumin, such as meringues.

As a thickening and/or gelling agent, (HP) can also be part of the composition of yoghurts.

In the abovementioned dietary applications, use is made in general of 0.01 to 5% by weight, and preferably between 0.05 and 2% by weight, of heteropolysaccharide (HP) with respect to the weight of the composition or formulation which contains it. Even more preferably, use is made of 0.1 to 1% by weight of heteropolysaccharide (HP) with respect to the weight of the composition or formulation.

It should be noted that the heteropolysaccharide (HP) does not modify the taste of the foods into which it is introduced.

The invention finally relates to the dietary compositions or formulations comprising the heteropolysaccharide (HP) as defined above.

The following examples illustrate the present invention without, however, limiting the scope thereof.

EXAMPLES

Example 1

This example describes the pure culturing of *Agrobacterium radiobacter* I-2001 (or DSM 12095), and the conditions for conserving the strain.

Pure Culturing of *Agrobacterium radiobacter* I-2001 (or DSM 12095)

The medium for maintaining the *Agrobacterium radiobacter* I-2001 (or DSM 12095) strain is Difco MY agar medium (reference 0712-01-8). The composition of this medium, already made up, is:

| | |
|---|---|
| bacto-yeast extract | 3 g |
| malt extract | 3 g |
| bacto-peptone | 5 g |
| bacto-dextrose | 10 g |
| bacto-agar | 20 g |

21 g of this medium is diluted in one liter of distilled water. After dissolution, the medium is sterilized in an autoclave for 15 minutes at 121° C. The medium is then distributed into Petri dishes.

The culturing is carried out on Petri dishes incubated at between 25° C. and 30° C., preferably between 25° C. and 28° C., for a minimum of 24 hours.

Preculturing—Conservation

The strain is then conserved in the form of tubes frozen at −196° C. by the process of liquid nitrogen freezing (LNF).

For liquid nitrogen freezing (LNF) a preculture is prepared on PYG10 medium having the following composition:

| | |
|---|---|
| malt extract | 3 g (obtained from Oxoïd) |
| yeast extract | 3 g (Oxoïd) |
| soya peptone | 5 g (Oxoïd) |
| glucose | 10 g (obtained from Prolabo) |
| mineral water qs 1 l. | |

For preparing the medium, all the ingredients are dispersed in the mineral water. The pH is adjusted to 6.5 with 10% $H_2SO_4$. The medium is sterilized for 20 minutes at 120° C. in an autoclave.

After incubation for 24 hours at 28° C. on a rotary shaker at 220 rpm and amplitude=50 mm, 10% by volume of pure sterile glycerol are added to the culture. The culture is then divided into cryotubes with capacities ranging from 1 ml to 10 ml, preferably from 2 ml to 4 ml.

These tubes are conserved in liquid nitrogen.

Example 2

This example describes the preparation and production of the heteropolysaccharide according to two fermentation processes, one with an organic source of nitrogen and the other with an inorganic source of nitrogen.

In this example, two "preculturing" steps are involved. These steps take place in 500 ml Erlenmeyer flasks, which corresponds to 100 ml of medium.

The production step, which corresponds to the step during which the bacterial strain produces the polysaccharide, takes place in a 20 liter fermenter in which 15 liters are usable.

The agitation conditions of the rotary shaker are: speed=220 rpm and amplitude=50 mm.

Preculturing Step 1

Preculturing step 1 is carried out with a PYG 10 medium having the following composition:

| | |
|---|---|
| malt extract | 3 g (Oxoïd) |
| yeast extract | 3 g (Oxoïd) |
| soya peptone | 5 g (Oxoïd) |
| glucose | 10 g (Prolabo) |
| distilled water qs 1 l. | |

All the ingredients are dispersed in a quantity of distilled water sufficient for 1 l. The pH is adjusted, before sterilization, to 6.5 with 10% $H_2SO_4$. The medium is sterilized for 20 minutes at 120° C. in an autoclave.

After sterilization and before inoculation with the cryotube (qs), the pH is at 7.33.

Each Erlenmeyer is seeded with a sufficient quantity of the LNF.

After incubation for 24 hours at 28° C. on a rotary shaker (220 rpm, A=50 mm), the medium has the following characteristics:
pH=6.82
viscosity=100 mPa·s
the population read on MY agar (Difco medium, reference 0712-01-8) after 72 hours at 28° C.=1.8×10$^9$ cfu/ml.

After incubation for 24 hours, preculture 1 is used to seed preculture 2.

Preculturing Step 2

Preculturing step 2 is carried out with a medium of the following composition:

| | | |
|---|---|---|
| yeast extract | 4 g | (Oxoïd) |
| $MgSO_4.7H_2O$ | 0.8 g | (Prolabo) |
| $FeSO_4.7H_2O$ | 0.01 g | (Prolabo) |
| $MnSO_4.H_2O$ | 5 ppm $Mn^{2+}$ | (Prolabo) |
| $K_2HPO_4$ | 4 g | (Prolabo) |
| or $Na_2HPO_4$ | 3 g | (Prolabo) |
| Glucose | 10 g | (Prolabo) |
| Deionized water qs 1 l | | (Prolabo) |

A solution of glucose at 100 g/l is prepared in distilled water and then sterilized at natural pH for 15 minutes at 121° C.

The remainder of the ingredients is dispersed in a quantity of deionized water sufficient for 900 ml, and then adjusted to pH 6.8 before sterilization for 15 minutes at 121° C.

After sterilization, 10 ml of the glucose solution are added to each Erlenmeyer.

After sterilization and before inoculation, the pH is 6.88.

Each Erlenmeyer is inoculated with the quantity sufficient for preculture 1.

After incubation for 24 hours at 28° C. on a rotary shaker (220 rpm, A=50 mm), the medium has the following characteristics:
pH=6.82
viscosity=50–100 mpa·s
the population read on MY agar (Difco medium, reference 0712-01-8) after 72 hours at 128° C.=1.6×10$^9$ cfu/ml.

After incubation for 24 hours, preculture 2 is used to seed the two fermentation media (fermenters 1 and 2) in the production step.

Production Step

The final step is the heteropolysaccharide (HP) production step.

The medium of fermenter 1 has the following composition:

| | | |
|---|---|---|
| Glucose | 20 g | (Prolabo) |
| CSL | 6 g | (Prolabo) |
| $MgSO_4.7H_2O$ | 0.8 g | (Prolabo) |
| $MnSO_4.H_2O$ | 5 ppm $Mn^{2+}$ | (Prolabo) |
| $K_2HPO_4$ | 1 g | (Prolabo) |
| Antifoam | 0.2 ml | |
| deionized water qs 1 l | | |

Glucose ⇒ the sufficient number of grams of glucose are dissolved in a quantity of deionized water sufficient for 3 l. The pH is lowered to 5 with 10% $H_2SO_4$. The solution is sterilized in a Mariotte flask for 30 minutes at 120° C. in an autoclave.

Nitrogen+salts ⇒ the sufficient number of grams of corn steep liquor (CSL), 15 g of $K_2HPO_4$, 12 g of $MgSO_4.7H_2O$, 23 ml of a solution of $MnSO_4.H_2O$ at 10 g/l and 3 ml of antifoam are dissolved in a quantity of deionized water sufficient for 7 l. The pH is adjusted to 6.5 with 10% $H_2SO_4$. This mixture is sterilized in situ for 30 minutes at 120° C.

1N sodium hydroxide ⇒ 40 g of NaOH chips are dissolved in a quantity of distilled water sufficient for 1 l. The solution is sterilized in a Mariotte flask for 30 minutes at 120° C. in an autoclave.

When all the ingredients are at 28° C., they are mixed in the fermenter. The fermenter is then inoculated with the qs of preculture 2.

The fermentation conditions in fermenter 1 are as follows:
Agitation ⇒ 200 rpm from 0 to 20 hours old, then 400 rpm until the end of fermentation.
Aeration ⇒ 400 l/h from 0 to 18 hours, and then 825 l/h from 24 hours until the end of fermentation.
The temperature is regulated at 28° C.
The pH is regulated at 6.8 with 1N NaOH.
The pressure is atmospheric pressure.
The medium of fermenter 2 has the following composition:

| | | |
|---|---|---|
| NaNO$_3$ | 1.2 g | (Prolabo) |
| NH$_4$NO$_3$ | 0.25 g | (Prolabo) |
| CaSO$_4$.2H$_2$O | 0.3 g | (Prolabo) |
| MgSO$_4$.7H$_2$O | 0.8 g | (Prolabo) |
| MnSO$_4$.H$_2$O | 5 ppm Mn$^{2+}$ | (Prolabo) |
| FeSO$_4$.7H$_2$O | 0.01 g | (Prolabo) |
| Na$_2$HPO$_4$ | 3 g | (Prolabo) |
| Glucose | 45 g | (Prolabo) |
| Antifoam | 0.2 ml | |
| Demineralized water qs 1 l | | |

Glucose ⇒ the sufficient number of grams of glucose are dissolved in a quantity of deionized water sufficient for 3 l. The pH is adjusted to 5 with 10% H$_2$SO$_4$. The solution is sterilized in a Mariotte flask for 30 minutes at 120° C. in an autoclave.
Nitrogen+salts ⇒ 18 g of NaNO$_3$, 3.75 g of NH$_4$NO$_3$, 4.5 g of CaSO$_4$.2H$_2$O, 23 ml of a solution of MnSO$_4$.H$_2$O at 10 g/l, 12 g of MgSO$_4$.7H$_2$O, 75 ml of a solution of FeSO$_4$.7H$_2$O at 2 g/l, 4.5 g of Na$_2$HPO$_4$ and 3 ml of antifoam are dissolved in a quantity of demineralized water sufficient for 7 l. The pH of this solution is adjusted to 6 with 10% H$_2$SO$_4$. This mixture is sterilized in situ for 30 minutes at 120° C.
1N sodium hydroxide ⇒ 40 g of NaOH chips are dissolved in a quantity of distilled water sufficient for 1 l.
The solution is sterilized in a Mariotte flask for 30 minutes at 120° C. in an autoclave.
When all the ingredients are at 28° C., they are mixed in the fermenter. The fermenter is then inoculated with the sufficient quantity of preculture 2.
The fermentation conditions in fermenter 2 are as follows:
Agitation ⇒ 200 rpm from 0 to 20 hours old, then 400 rpm until the end of fermentation.
Aeration ⇒ 400 l/h from 0 to 24 hours, and then 825 l/h from 24 hours until the end of fermentation.
The temperature is regulated at 28° C.
The pH is regulated at 6.8 with 1N NaOH.
The pressure is atmospheric pressure.
Fermentation Results
Depending on the culture medium studied, the fermentation durations range from 65 to 90 hours, the solids which can be precipitated with isopropanol range from 15 to 26 g/kg and the weight yield with respect to the source of carbon used ranges from 33 to 60%.
Extraction and Purification
The end-of-fermentation must is stabilized with 10% (weight/weight) of pure isopropanol. It is then heat-treated at 110° C. for 25 minutes at natural pH (herein, pH=7). The pH during the heat treatment does not vary.
Once the heat treatment is over, the must is extracted while hot (temperature>80° C.).
The precipitation conditions are:
isopropanol=53% weight/weight
Na$_2$SO$_4$=0.2% weight/weight
solids=0.4% weight/weight.

After precipitation, the fibers are chopped up and then washed and dehydrated with isopropanol having a titer of 78%.
The fibers are then dried in a ventilated incubator at 80–85° C. until a product is obtained which has a water content of approximately 10% by weight.
The fibers are then ground and sieved.

Example 3

The subject of this example is the use of (HP) obtained in example 2, in a dietary formulation for topping.
In the examples which will follow, the flow viscosities, expressed in mpa·s, were measured using a BROOKFIELD RVT 20-2 viscosimeter, at room temperature.
The values of the elastic moduli, expressed in Pa, were produced using a CARRIMED CSL 100 controlled stress rheometer. They were measured in an oscillatory system—frequency of 0.01 to 10 Hz.
The measurements of degree of overrunning, expressed as %, were carried out in the following way:
the mousse is introduced into a beaker of volume (V) and of known mass; the beaker is given three sharp taps, and the mousse is leveled;
the beaker is weighed in order to determine the mass (M) of mousse that it contains;
the degree of overrunning=[M(g)/V(ml)]×100
Two formulations are prepared:
formulation 3.1: comprising the heteropolysaccharide (HP) according to the invention,
formulation 3.2 (comparative): comprising sodium caseinate and sodium alginate.
The compositions of the formulations are given in table I.

TABLE I

| Components | Formulation 3.1 (% by weight) | Formulation 3.2 (% by weight) |
|---|---|---|
| Oily phase | | |
| Hydrogenated palm oil | 7.6 | 7.6 |
| Monodiglyceride acetic ester | 0.76 | 0.76 |
| Monodiglyceride lactic ester | 0.76 | 0.76 |
| Aqueous phase | | |
| Sugar | 8.35 | 8.35 |
| Powdered skimmed milk | 7.44 | 7.44 |
| Maltodextrin (Glucidex ® 19) | 4.6 | 4.6 |
| Sodium caseinate | — | 1.5 |
| Sodium alginate | 1 | 0.02 |
| Heteropoly-saccharide (HP) | 1 | — |
| Water | qs 100 | qs 100 |

Aqueous Phase
In a beaker equipped with a deflocculating paddle, the amount of water required is weighed and the mixture of powders described in the table above is dispersed with vigorous stirring (500 rpm).
The stirring is maintained for 5 minutes after the introduction of said powders.
Oily Phase
In a beaker, the fatty substance and the emulsifiers are heated, in a water bath, to 70° C.
The oily phase is then added to the aqueous phase with stirring at 1000 rpm.

The stirring is maintained for 5 minutes after the introduction of the oily phase. During this operation, the water evaporation is compensated.

The entire mixture is then homogenized using an Ultra-Turrax for 2 minutes at 2000 rpm.

The mixture is cooled to a temperature lower than 10° C., before carrying out the overrunning. This takes place using a laboratory mixer of KENWOOD CHEF type, at maximum speed for 3 minutes at a temperature close to 5° C.

The results are given in table II.

TABLE II

|  | Formulation 3.1 | Formulation 3.2 |
|---|---|---|
| Viscosity before overrunning (mPa · s) | 1500 | 1700 |
| Degree of overrunning (%) | 350 | 250 |
| G' measured at 1 Hz (Pa) | 1800 | 1600 |
| G" measured at 1 Hz (Pa) | 300 | 400 |

These results show that formulation 3.1, which uses the (HP) according to the invention, has a lower viscosity than that of comparative formulation 3.2 and, because of this, is easier to overrun.

In addition, formulation 3.1 (according to the invention) is firstly more gelled (higher G' at high frequency), and has an improved degree of overrunning.

What is claimed is:

1. A heteropolysaccharide (HP) obtained by fermentation of a medium comprising at least one *Agrobacterium radiobacter* I-2001 strain, a recombinant thereof or mutant thereof, and a source of carbon assimilable by said strain, a recombinant thereof or a mutant thereof.

2. A heteropolysaccharide (HP) as claimed in claim 1, wherein said heteropolysaccharide comprises glucose units, galactose units, glucuronic acid units, acetic acid units, and pyruvic acid units.

3. A heteropolysaccharide (HP) as claimed in claim 1, wherein molar proportions of units are as follows in reference to glucose units being equal to 1:

galactose units: 0.2–5, glucuronic acid units: 0.1–3, acetic acid units: 0–5, and pyruvic acid units: 0.01–2.

4. A heteropolysaccharide (HP) as claimed in claim 3, wherein said molar proportions are as follows:

galactose units: 0.8–2, glucuronic acid units: 0.4–1, acetic acid units: 0–3, and pyruvic acid units: 0.01–2.

5. A heteropolysaccharide (HP) as claimed in claim 2, wherein the glucuronic units, the acetic acid units and the pyruvic acid units are in the form of salts.

6. A heteropolysaccharide (HP) as claimed in the preceding claim, wherein said acids are in the form of sodium, potassium, calcium or ammonium salts.

7. A heteropolysaccharide (HP) as claimed in claim 1, having a mean molar mass by weight (Mw) of between $1 \times 10^5$ and $8 \times 10^6$ g/mol.

8. A heteropolysaccharide (HP) as claimed in claim 7, having a mean molar mass of between $8 \times 10^5$ and $5 \times 10^6$ g/mol.

9. A heteropolysaccharide (HP) as claimed in claim 8, having a mean molar mass by weight (Mw) of about $3 \times 10^6$ g/mol.

10. A heteropolysaccharide (HP) as claimed in claim 7, having an elastic modulus of between 0.1 and 200 Pa and a viscous modulus of between 0.1 and 20 Pa, measured in a 1% weight/weight solution in distilled water at 23° C. with a controlled stress rheometer in oscillatory mode at 1 Hz.

11. A heteropolysaccharide (HP) as claimed in claim 10, wherein the elastic modulus is of between 20 and 200 Pa and the viscous modulus is of between 0.5 and 15 Pa.

12. A heteropolysaccharide (HP) as claimed in claim 11, wherein the elastic modulus is of between 20 and 150 Pa and the viscous modulus is of between 0.5 and 10 Pa.

13. A heteropolysaccharide (HP) as claimed in claim 12, wherein the elastic modulus is of about 100 Pa and the viscous modulus is of about 5 Pa.

14. A heteropolysaccharide (HP) as claimed in claim 1, wherein a 1% weight/weight solution of said HP in distilled water containing 1% weight/weight of NaCl, at 23° C., produces a flow viscosity value, at a shear rate of 0.1 s$^{-1}$, of between 100 and 5000 Pa·s.

15. A heteropolysaccharide (HP) as claimed in claim 1, wherein 1% weight/weight solution of said HP in distilled water containing 1% weight/weight of NaCl, at 23° C., produces a flow viscosity value, at a shear rate of 10 s$^{-1}$, of between 0.5 and 300 Pa·s.

16. A heteropolysaccharide (HP) as claimed in claim 1, being in the form of fiber or powder.

17. A process for preparing the heteropolysaccharide (HP) as defined in claim 1, comprising the steps of:

a) fermenting a medium comprising at least one *Agrobacterium radiobacter* I-2001 strain, a recombinant thereof or mutant thereof, and a source of carbon assimilable by said strain, a recombinant thereof or a mutant thereof, b) separating a heteropolysaccharide (HP) from a fermentation medium according to the following steps:

aa) at the end of fermentation, the medium is subjected to heat treatment between 80° C. and 120° C. for 10 to 60 minutes to obtain a heteropolysaccharide in the medium, bb) the heteropolysaccharide (HP) obtained in step aa) is precipitated using a water-miscible organic liquid, and cc) the heteropolysaccharide (HP) obtained in step bb) is separated from the organic liquid.

18. A process as claimed in claim 17, wherein, in step aa), the heteropolysaccharide in the medium has a pH of between 6 and 8.

19. A process as claimed in claim 17, wherein the medium must obtained in step aa) is maintained at a temperature identical to the temperature of the heat treatment.

20. A process as claimed in claim 17, wherein, in step bb), the precipitation of the heteropolysaccharide (HP) with an organic liquid is carried out in the presence of sodium, potassium or calcium sulfates, chlorides or phosphates salts.

21. A process as claimed in claim 17, wherein, in step bb), the precipitation takes place at a temperature of between 40 and 60° C.

22. A process as claimed in claim 17, wherein the heteropolysaccharide obtained at the end of step cc) is in the form of fibers which are dehydrated.

23. A process as claimed in claim 22, wherein the fibers are dried, ground or sieved so as to obtain a heteropolysaccharide (HP) powder.

24. A thickening or gelling agent comprising the heteropolysaccharide (HP) as defined in claim 1.

25. A petroleum, agrochemical, food, cosmetic, paint, contact lense, glues, ink, household cleaner, or industrial cleaner product comprising the heteropolysaccharide (HP) as defined in claim 1.

26. A dietary formulations comprising the heteropolysaccharide (HP) as defined in claim 1 in amounts of between 0.01 and 5% by weight, of heteropolysaccharide (HP) with respect to the weight of the composition or formulation.

27. A heteropolysaccharide (HP) as claimed in claim 1, wherein said heteropolysaccharide consists essentially of glucose units, galactose units, glucuronic acid units, acetic acid units, and pyruvic acid units.

28. A heteropolysaccharide (HP) as claimed in claim 27, wherein molar proportions of units are as follows in reference to glucose units being equal to 1:

galactose units: 0.8–2, glucuronic acid units: 0.4–1, acetic acid units: 0–3, and pyruvic acid units: 0.01–2.

* * * * *